(12) United States Patent
Beals (10) Patent No.: US 12,072,303 B2
(45) Date of Patent: Aug. 27, 2024

(54) PROCESS FOR NON-DESTRUCTIVE QUALITY CONTROL INSPECTION OF SELF-PIERCING RIVET (SPR) JOINTS

(71) Applicants: Randy S. Beals, Grand Ledge, MI (US); MAGNA INTERNATIONAL INC., Aurora (CA)

(72) Inventor: Randy S. Beals, Grand Ledge, MI (US)

(73) Assignee: MAGNA INTERNATIONAL INC., Aurora (CA)

( * ) Notice: Subject to any disclaimer, the term of this patent is extended or adjusted under 35 U.S.C. 154(b) by 283 days.

(21) Appl. No.: 17/637,250

(22) PCT Filed: Aug. 26, 2020

(86) PCT No.: PCT/US2020/047857
§ 371 (c)(1),
(2) Date: Feb. 22, 2022

(87) PCT Pub. No.: WO2021/041449
PCT Pub. Date: Mar. 4, 2021

(65) Prior Publication Data
US 2022/0341857 A1 Oct. 27, 2022

Related U.S. Application Data

(60) Provisional application No. 62/892,668, filed on Aug. 28, 2019.

(51) Int. Cl.
*G01N 23/046* (2018.01)
*B21J 15/02* (2006.01)

(52) U.S. Cl.
CPC .......... *G01N 23/046* (2013.01); *B21J 15/025* (2013.01)

(58) Field of Classification Search
CPC ............................ G01N 23/046; B21J 15/025
See application file for complete search history.

(56) References Cited

U.S. PATENT DOCUMENTS

| 10,871,591 B2 * | 12/2020 | Atherton ................. G01V 5/20 |
| 2003/0161436 A1 | 8/2003 | Boyd et al. |
| 2013/0051516 A1 | 2/2013 | Yang et al. |

(Continued)

*Primary Examiner* — David P Porta
*Assistant Examiner* — Fani Polyzos Boosalis
(74) *Attorney, Agent, or Firm* — Dickinson Wright PLLC (57) ABSTRACT

A system and method for inspecting an assembly including components joined by self-piercing rivets by a computerized tomography (CT) scan of the joint is provided. The system includes a source of x-rays, a mounting unit for an assembly including the joint which is subject to the x-rays, and an x-ray detector disposed opposite the source for detecting the x-rays. The x-rays are provided at a high energy level of at least 200 kV to generate images having a resolution of at least 200 micrometers (μm). A computer stitches the images together to form reconstructive images which show details of the joint. The assembly to be inspected is not destroyed or modified prior to the inspection process. The resolution of the images generated by the x-rays is high enough to determine the presence of cracks, if any, the interlock ($S_H$), minimum thickness ($T_{min}$), and overall structure of the unmodified assembly.

18 Claims, 7 Drawing Sheets

(56) References Cited

U.S. PATENT DOCUMENTS

| | | |
|---|---|---|
| 2014/0259600 A1 | 9/2014 | Kilibarda et al. |
| 2016/0252468 A1 | 9/2016 | Lou et al. |
| 2017/0234837 A1 | 8/2017 | Hall et al. |
| 2018/0117666 A1 | 5/2018 | Trinick |

* cited by examiner

| Parameters | Value | Units |
|---|---|---|
| Kilovolts | 225 | (kV) |
| Milliamps | 321 | (uA) |
| Focal Spot Size | 72 | (μm) |
| Resolution | 200 | (μm) |
| Active Area | 16" x 16" | (in x in) |
| Magnification | 2.2 | |
| Integration Time | 1 | s (seconds) |
| Frame Average | 2 | n/a |
| CU Filter | none | n/a |
| Projections | 1600 | |
| ODD (Object to Detector) | 657.5 | (mm) |
| SDD (Source to Detector) | 1191 | (mm) |
| SOD (Source to Object) | 533.5 | (mm) |

PROCESS FOR NON-DESTRUCTIVE QUALITY CONTROL INSPECTION OF SELF-PIERCING RIVET (SPR) JOINTS

CROSS-REFERENCE TO RELATED APPLICATIONS

This U.S. National Stage Patent Application claims the benefit of PCT International Patent Application Serial No. PCT/US2020/047857 filed Aug. 26, 2020 entitled "PROCESS FOR NON-DESTRUCTIVE QUALITY CONTROL INSPECTION OF SELF-PIERCING RIVET (SPR) JOINT" which claims the benefit of and priority to U.S. Provisional Patent Application Ser. No. 62/892,668 filed on Aug. 28, 2019, and titled "Process For Non-Destructive Quality Control Inspection Of Self-Piercing Rivet (SPR) Joint"," the entire disclosures of which are hereby incorporated by reference.

BACKGROUND OF THE INVENTION

1. Field of the Invention

The invention relates to a method for inspecting an assembly including at least two components joined by a rivet, and a system for inspecting the assembly including at least two components joined by the rivet.

2. Related Art

Inspection of a joint between metal components is oftentimes required to determine the quality of the joint. For example, automotive vehicle components joined by self-piercing rivets (SPR) are typically inspected for quality control. The method used to inspect the joint typically includes cutting through the joint, polishing the cut joint so that a cross-section of the joint is visible, and then taking images of the joint at a high resolution for analysis. Improved inspection techniques which require less time and expense are desired.

SUMMARY

This section provides a general summary of the inventive concepts associated with this disclosure and is not intended to be interpreted as a complete and comprehensive listing of all of its aspects, objectives, features, and advantages.

It is an aspect of the subject invention to provide a method of inspecting an assembly including at least a first component and a second component joined by a rivet. The method includes scanning a portion of the assembly which includes the rivet joining the first component to the second component with computerized tomography (CT).

Another aspect of the invention provides a system for inspecting an assembly including at least a first component and a second component joined by a rivet. The system comprises a source of x-rays and an x-ray detector. The source of x-rays emits the x-rays toward a portion of the assembly which includes the rivet at an energy level of at least 200 kV.

The system and method of the present invention are able to provide for improved quality control at a relatively low cost. An advantage over other inspection methods is that the assembly to be inspected does not need to be destroyed or modified prior to inspection. Thus, the system and method of the present invention create less scrap, which saves energy and costs, and provides for more accurate inspection of each assembly produced.

BRIEF DESCRIPTION OF THE DRAWINGS

The drawings described herein are for illustrative purposes only of selected embodiments and are not intended to limit the scope of the present disclosure. The inventive concepts associated with the present disclosure will be more readily understood by reference to the following description in combination with the accompanying drawings wherein.

DESCRIPTION OF EXAMPLE EMBODIMENTS

Example embodiments will now be described more fully with reference to the accompanying drawings. However, the example embodiments are only provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Figures 1, 1A:
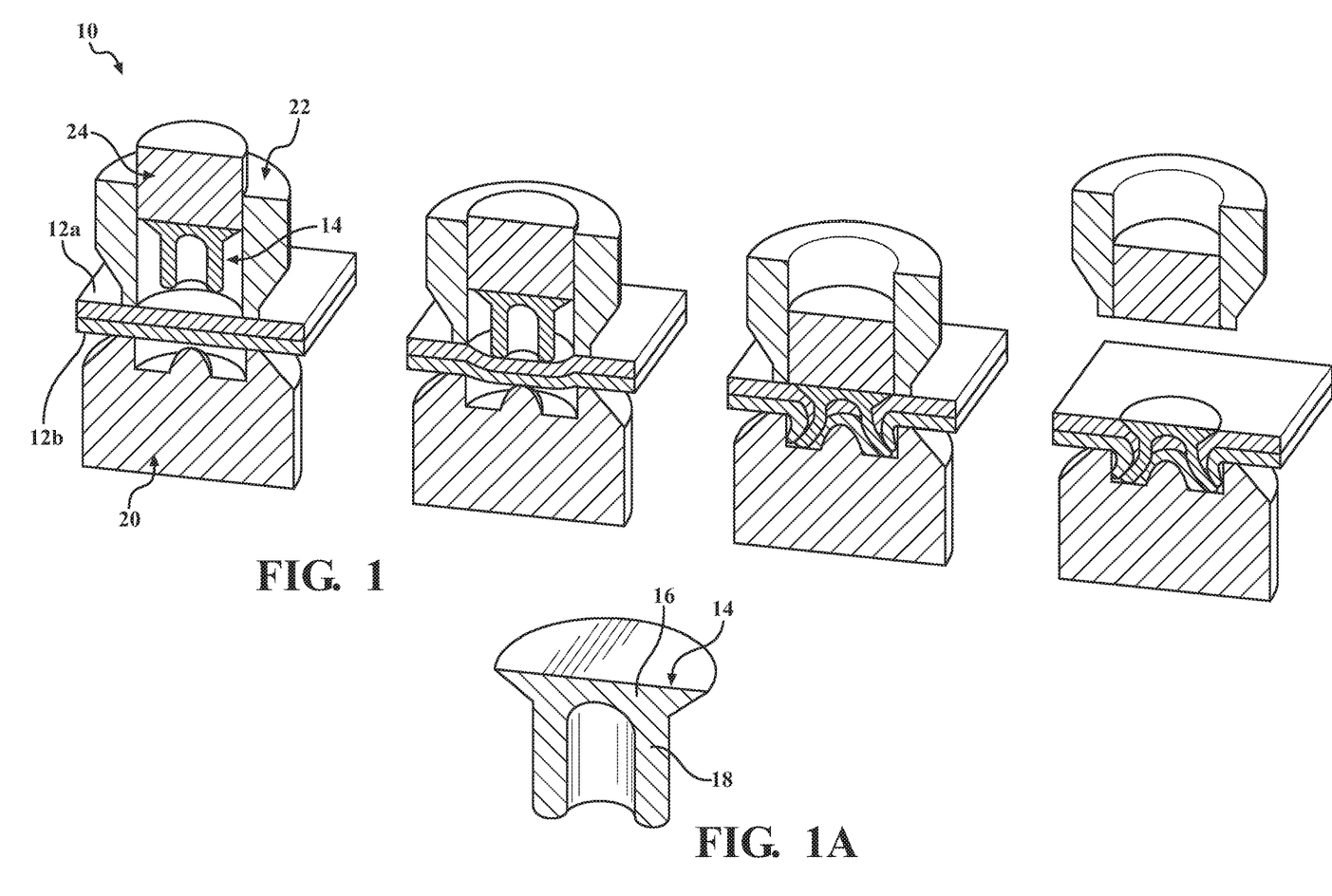
FIG. 1 illustrates a process of joining two components by a self-piercing rivet according to an example embodiment.
FIG. 1A illustrates the rivet before the rivet is inserted into the components.

The invention provides a system and method for inspecting an assembly 10 including at least two components 12a, 12b joined by at least one self-piercing rivet 14 by performing a computerized tomography (CT) scan of the joint. An example of a riveting process that can be used to form the assembly 10 to be inspected is shown in FIG. 1. In this case, the assembly 10 includes two of the components 12a, 12b which are sheets of metal, and the self-piercing rivets 14 joining the two components 12a, 12b. A top one of the components 12a is formed of steel, a bottom one of the components 12b is formed of aluminum, and the rivet 14 is formed of steel. However, the components 12a, 12b and rivets 14 could be formed of different materials, and the assembly 10 could alternatively include three or more components 12a, 12b formed of various different materials and/or dimensions. Various different types of assemblies 10 can be inspected using the method described herein; the designs, dimensions, and materials can vary. According to an example embodiment, the first component 12a is a cast front shock tower formed of an aluminum alloy, for example Aural 2 at T7 temper or Aural 5S in either F Temper or T81 (after paint bake); the second component 12b is a front rail formed of steel, for example DP 580; and the rivet 14 is also formed of steel.

Figure 2:
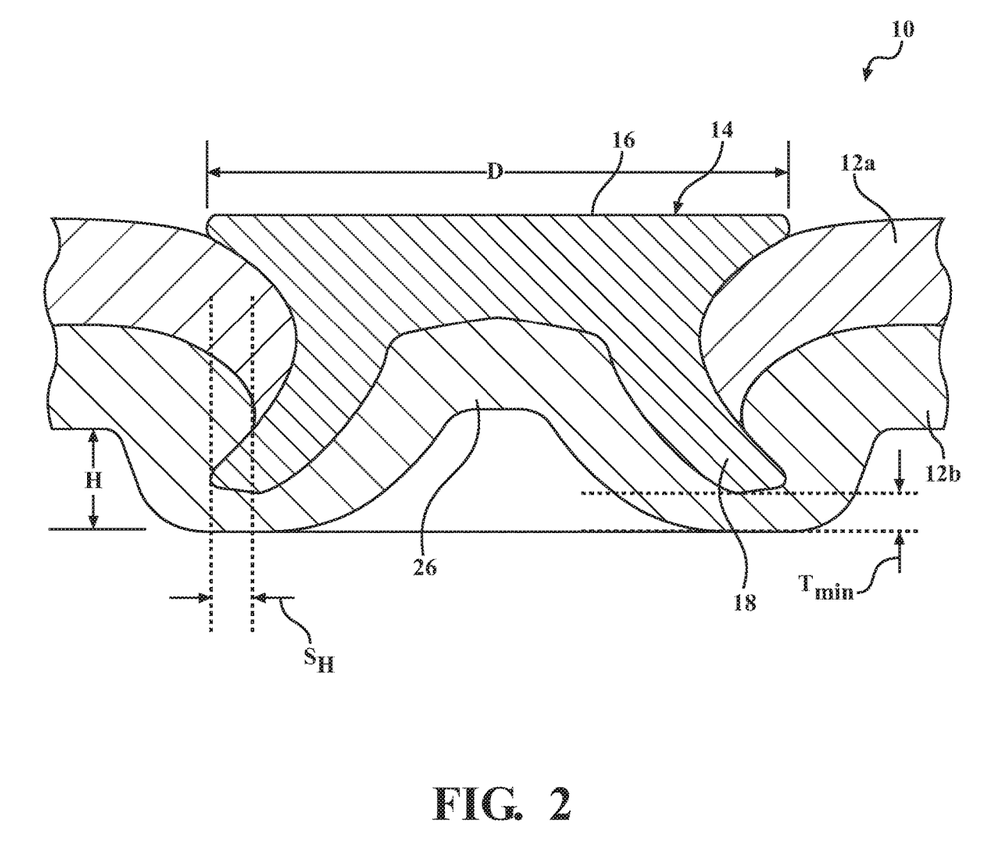
FIG. 2 is a cross-section of two components joined by a self-piercing rivet for inspection according to an example embodiment.

As shown in FIGS. 1A and 2, the rivet 14 includes a head 16 and a tubular-shaped base 18, also referred to as legs, depending from the head 16, but the design and dimensions of the rivet 14 can change. FIG. 1A illustrates the rivet 14 before the rivet 14 is inserted into the components 12a, 12b, and FIG. 2 illustrates the rivet 14 after the rivet 14 joins the components 12a, 12b. Also, the components 12a, 12b can be joined by a single rivet 14, but typically the components 12a, 12b are joined by multiple rivets 14.

The example process of FIG. 1 includes disposing the components 12a, 12b to be joined on a die 20. The die 20 includes a slot for receiving the rivet 14 and at least a portion of the components 12a, 12b. The system used to pierce the components 12a, 12b further includes a blank holder 22 disposed above the components 12a, 12b to be joined. The blank holder 22 includes a slot receiving a punch 24 and the rivet 14. During operation, the blank holder 22 rests on the components 12a, 12b to be joined, and the punch 24 presses the rivet 14 into the components 12a, 12b. The rivet 14 pierces the first component 12a and pierces through a portion of the second component 12b, but does not pierce entirely through the second component 12b. The base (legs) 18 of the rivet 14 should not be visible by inspecting the exterior of the components 12a, 12b forming the assembly 10 with the naked eye.

FIG. 2 illustrates a cross-section of the rivet 14 of the assembly 10 which can be inspected by the method disclosed herein. The inspection method can be used to determine various dimensions and features of the assembly 10. The method can be used to identify the location of the components 12a, 12b, the base 18 and the head 16 of the rivet 14, a diameter D of the head of the rivet 14, a slug 26 formed by the bottom component 12b. According to one embodiment, the method can be used to measure an interlock $S_H$ and minimum thickness $T_{min}$, which are identified in the example of FIG. 2. The interlock $S_H$ is a radial distance between a top end of the base 18 and the outermost portion of the base 18 of the rivet 14. The minimum thickness $T_{min}$ is the distance between the bottom end of the lowermost surface of the rivet 14 and the exterior surface of the lowest component 12b joined by the rivet 14. The method can also be used to measure a height of a button, referred to as a button height H, which is present in the finished assembly 10, as shown in FIG. 2. The button height H is the distance between a bottom flat surface of the bottom component 12b (which is located radially outward of the rivet 14) and a lowermost surface the bottom component 12b (which is located directly beneath the river 14). Destruction of the assembly 10, for example to obtain a cross-section of the assembly 10, which occurs in other methods and previously occurred to obtain the cross-section of FIG. 2, is not required according to the method of the present invention.

Figure 3:
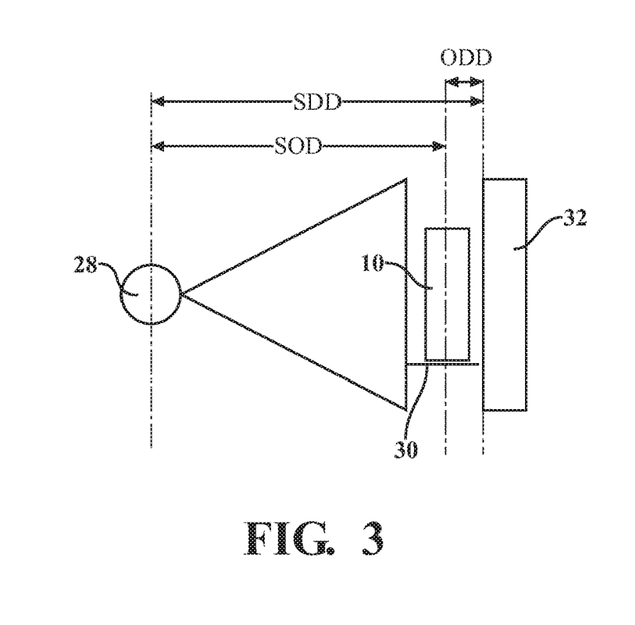
FIG. 3 illustrates a system for inspecting an assembly including at least two components joined by at least one self-piercing rivet according to an example embodiment.

A system which can perform the method, including a computerized tomography (CT) scan, is shown in FIG. 3. The system generally includes a source of x-rays 28, a mounting unit 30 for holding the assembly 10 including the joint (object to be inspected) which is subject to the x-rays, and an x-ray detector 32 disposed opposite the source 28 for detecting the x-rays from a tungsten film. The mounting unit 30 is located between the source of x-rays 28 and the x-ray detector 32. The x-rays are emitted at a high energy level of at least 200 kV, for example 200 kV to 300 kV, with a current of at least 200 milliamp ($\mu A$), in order to generate high resolution images of the assembly 10. The images typically have a resolution of at least 150 micrometers ($\mu m$), for example 150 to 300 $\mu m$, or at least 200 $\mu m$.

Figure 4:
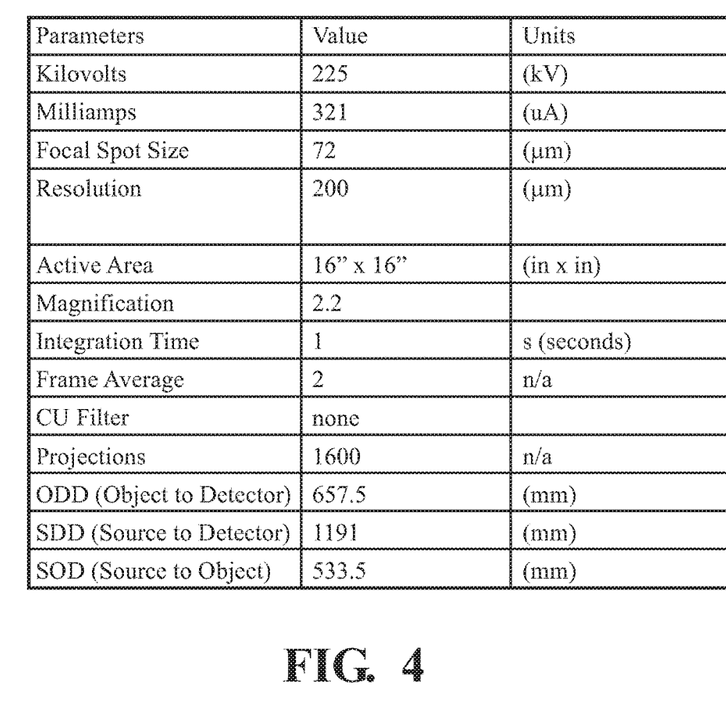
FIG. 4 includes a Table listing geometry and parameters of an inspection process according to an example embodiment.
Figure 5:
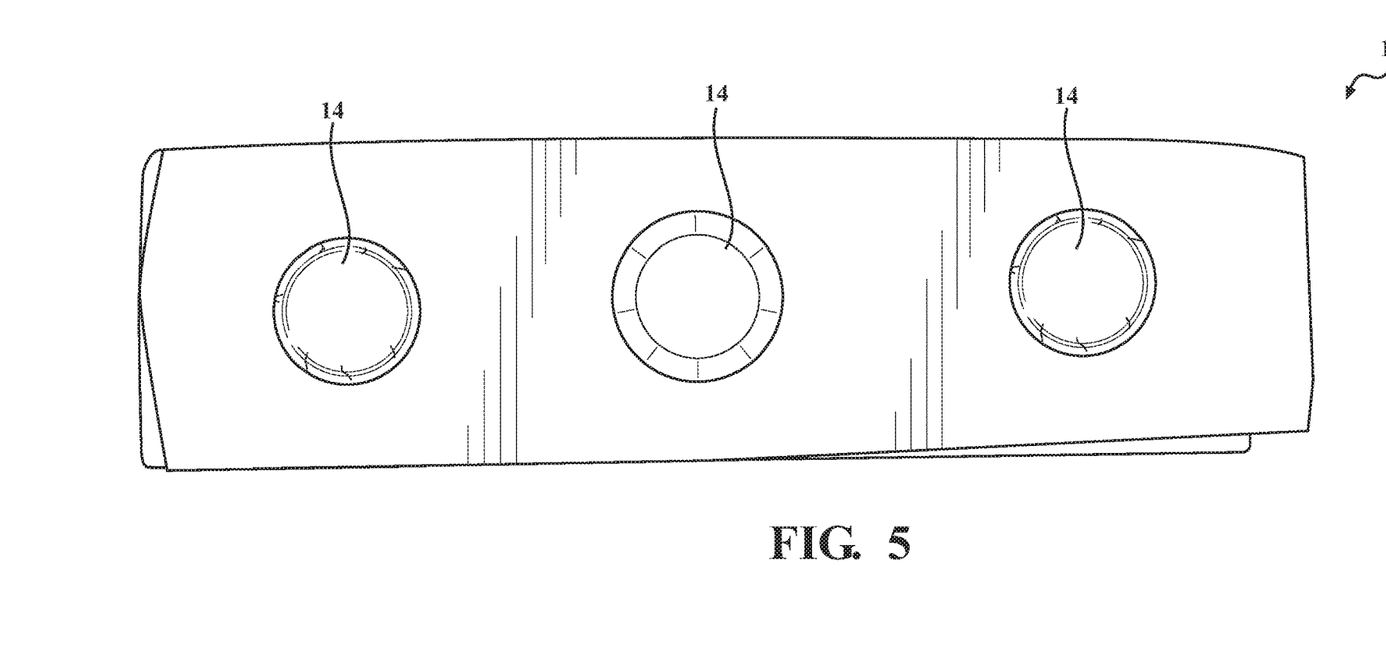
FIG. 5 is a top view image of components joined by self-piercing rivets, wherein the image is obtained by a CT scan according to an example embodiment.
Figure 6:
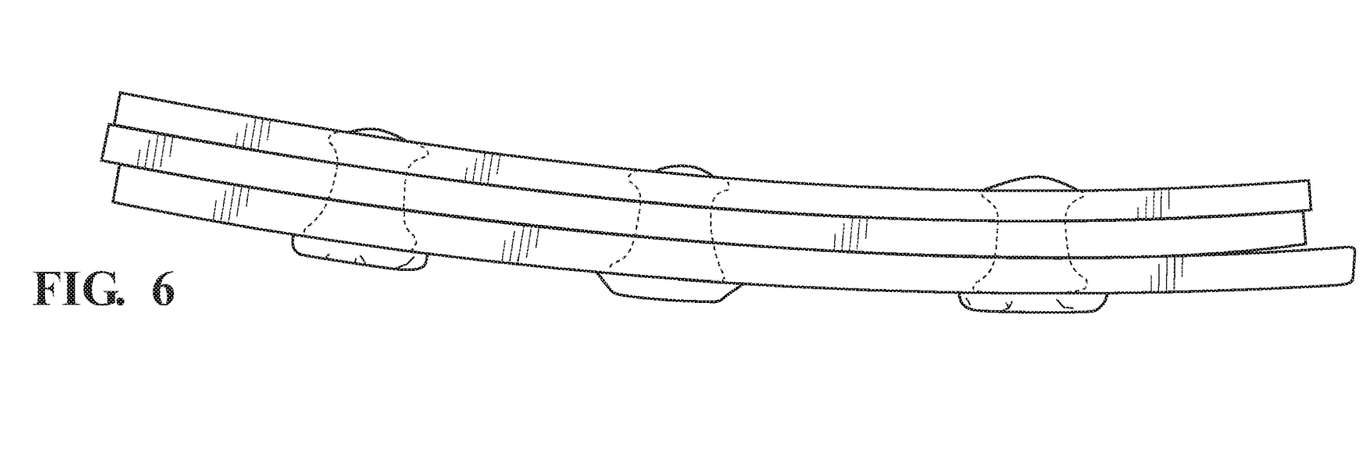
FIG. 6 is a side view image of the components of FIG. 5.
Figure 7:
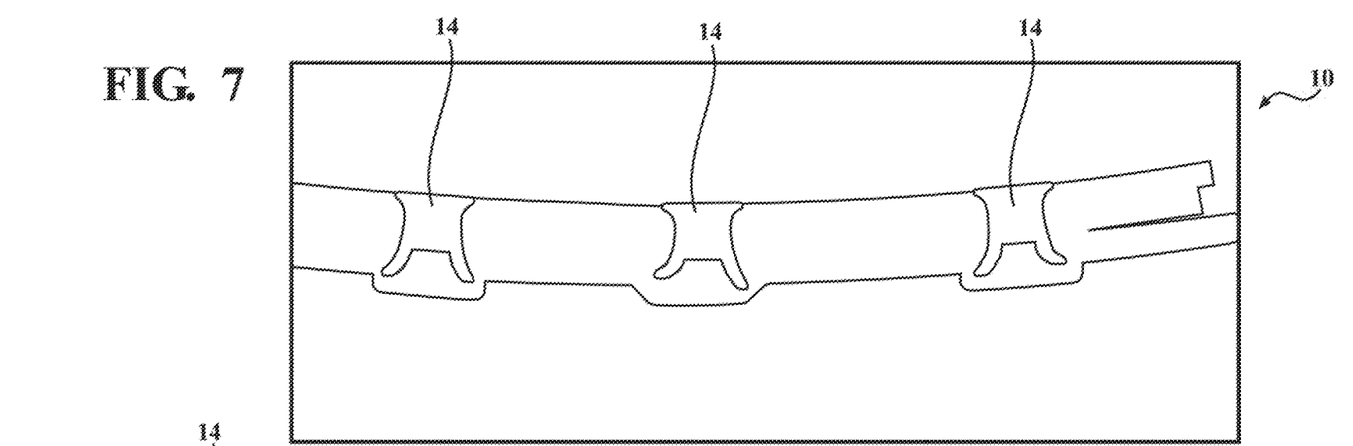
FIGS. 7-9 are cross-sectional view images of components joined by self-piercing rivets, wherein the images are obtained by a CT scan according to example embodiments.
Figure 8:
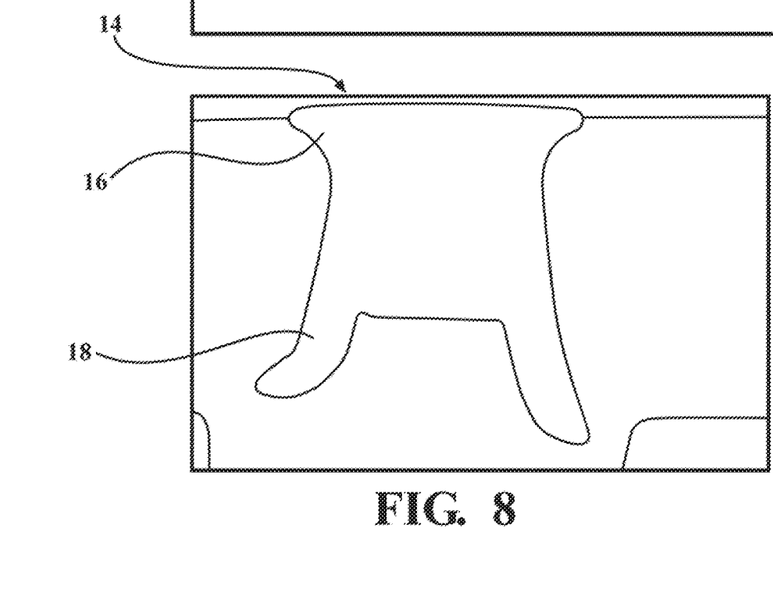
Figure 9:
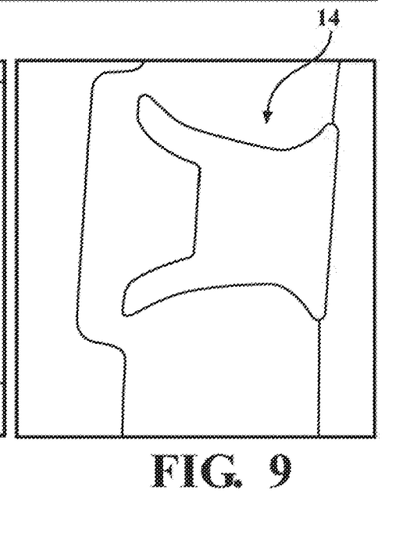

FIG. 4 lists imaging geometry and parameters of the system performing the CT scan according to an example embodiment. However, the imaging geometry and parameters can vary. In the example embodiment, the x-rays are provided at an energy level of 225 kV. However, the energy level of the example embodiment could vary by +/−12%; for example, the energy level could range from 200 kV to 225 kV. The current of the x-rays is provided at 321 $\mu A$. However, the current of the example embodiment could vary by +/−8%; for example, the current could range from 300 $\mu A$ to 325 $\mu A$. The system of the example embodiment has a focal spot size of 72 $\mu m$. However, the focal spot size of the example embodiment could vary by +/−4%; for example, the focal spot size could range from 69 $\mu m$ to 72 $\mu m$. The images generated by the system of the example embodiment have a resolution of 200 $\mu m$. However, the maximum achievable resolution of the example embodiment could vary by +/−4%; for example, the voxel size resolution could range from 69 $\mu m$ to 72 $\mu m$. The active area of the example system, which is defined as the total area of the assembly 10 imaged, is 16 inches×16 inches. However, the active area of the example embodiment could vary by +/−180%; for example, the active area could range from 726 mm to 1050 mm. The magnification of the example embodiment is 2.2. However, the magnification of the example embodiment could vary by +/−130%; for example, the magnification could range from 2× to 10×. The integration time of the example embodiment, which is defined as the total scan time for performing a scan must take into consideration the additional image reconstruction time when determining how quickly the image(s) may be viewed, is 1 second. However, the integration time of the example embodiment could vary by +/−190%; for example, the integration time could range from 1 second to 60 seconds. The frame average of the example embodiment, which is defined as a method to balance the exposure time and signal to noise ratio (SNR), is 2. However, the frame average of the example embodiment could vary by +/−130%; for example, the frame average could range from 2 to 10. The example system does not includes a copper (Cu) prefilter. However, a copper prefilter could be used. The CT scan of the example embodiment includes 1600 projections. However, the number of projections could vary by +/−29%; for example, the number of projections could range from 1200 to 1600. In the example system, the distance from the assembly 10 to the detector 32 is 657.5 mm. However, the distance from the assembly 10 to the detector 32 could vary by +/−33%; for example 500 mm to 700 mm. In the example system, the distance from the source 28 to the detector 32 is 1191 mm. However, the distance from the source 28 to the detector 32 could vary by +/−40%; for example 1000 mm to 1500 mm. In the example system, the distance from the source 28 to the assembly 10 is 533.5 mm. However, the distance from the source 28 to the assembly 10 could vary by +/−18%; for example, 500 mm to 600 mm. Features as small as 300 μm or less, 200 μm or less, or 100 μm or less can be identified in the images obtained by the system of the example embodiment. A computer stitches or combines the images together to form reconstructive images which show details of the assembly 10 with the joint to be inspected. A reconstructive image can be referred to as a combined image which has a resolution of at least 150 μm, or at least 200 μm.

FIGS. 5-12 are x-ray images of the assembly 10 including the components 12 joined by the self-piercing rivet 14 which were obtained by the system and method according to example embodiments. An advantage of the system and method disclosed herein is that the assembly 10 does not need to be destroyed or modified, for example to obtain a cross-section of the assembly 10, prior to inspection. Thus, the system and method creates less scrap, which saves energy and costs, and provides for more accurate inspection of each assembly 10 produced.

Figure 10:
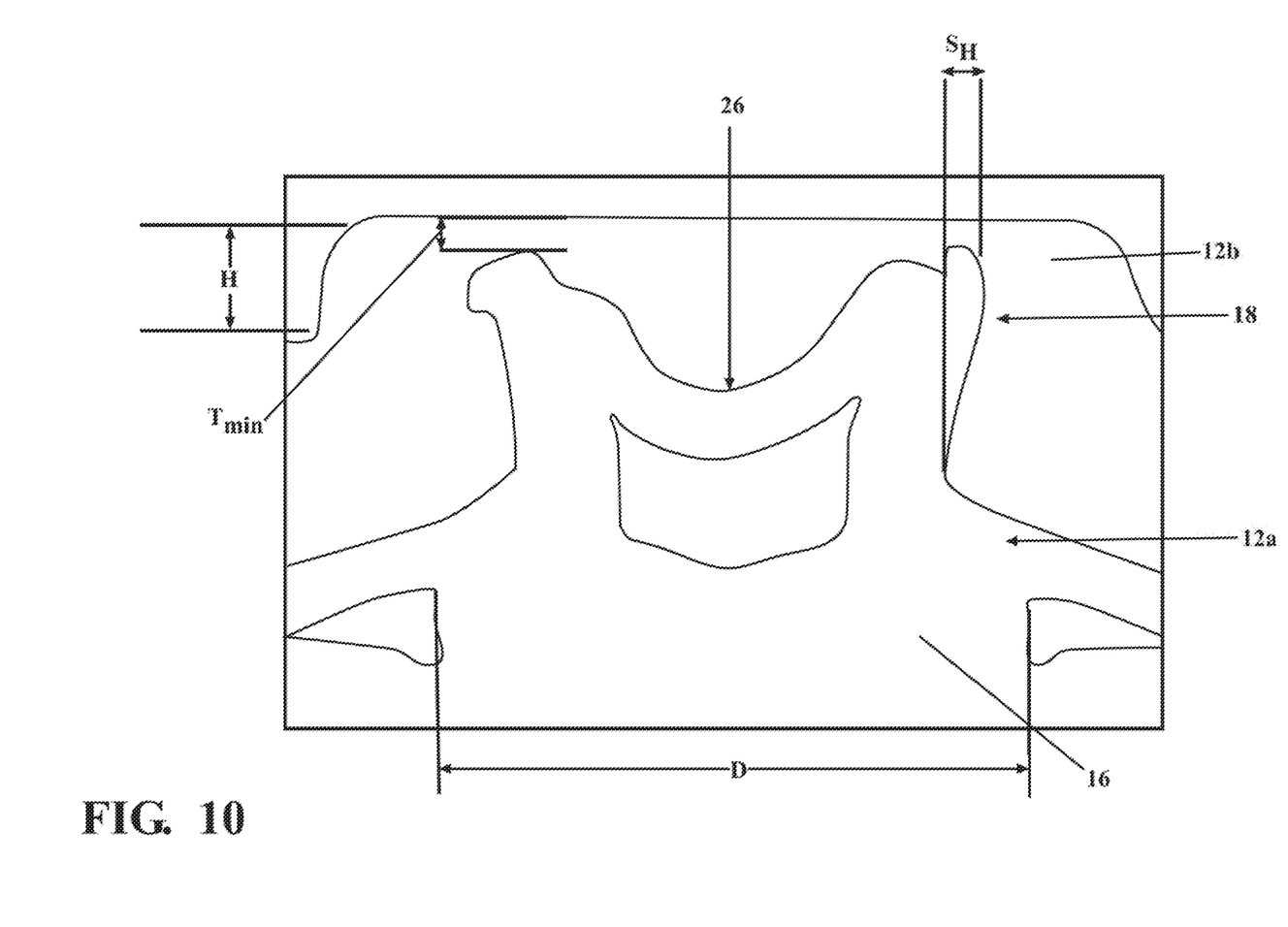
FIG. 10 is another cross-sectional view image of two components joined by a self-piercing rivet, wherein the image is obtained by a CT scan according to an example embodiment, and the Figure identifies the two components, head and base of the rivet, a button height, interlock, minimum thickness, slug, and head diameter.
Figure 11:
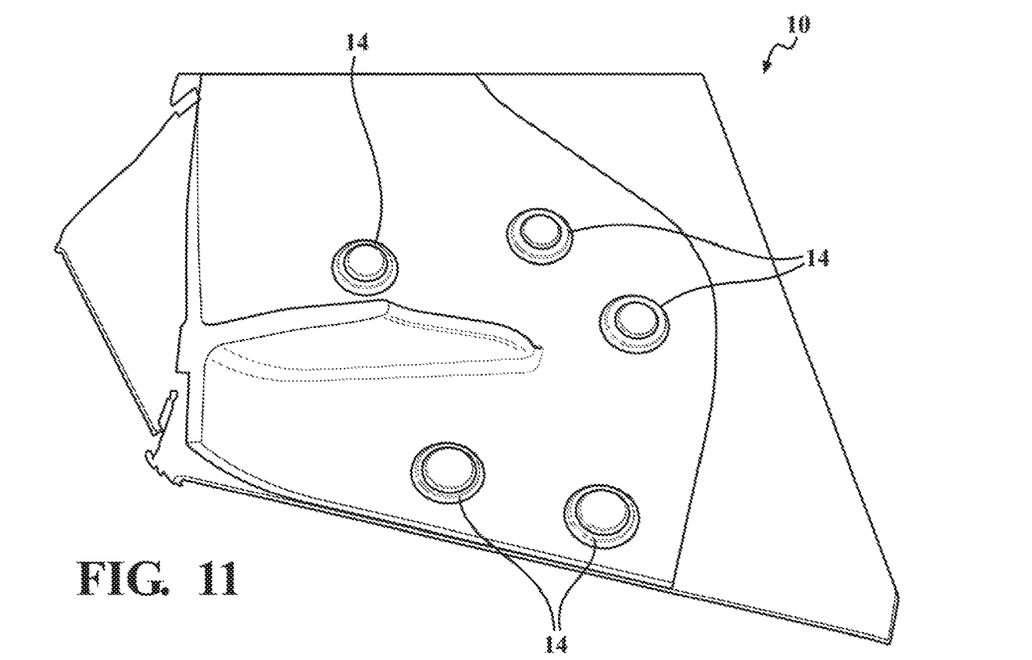
FIGS. 11 and 12 are perspective view images of components joined by self-piercing rivets, wherein the images are obtained by a CT scan according to example embodiments.
Figure 12:
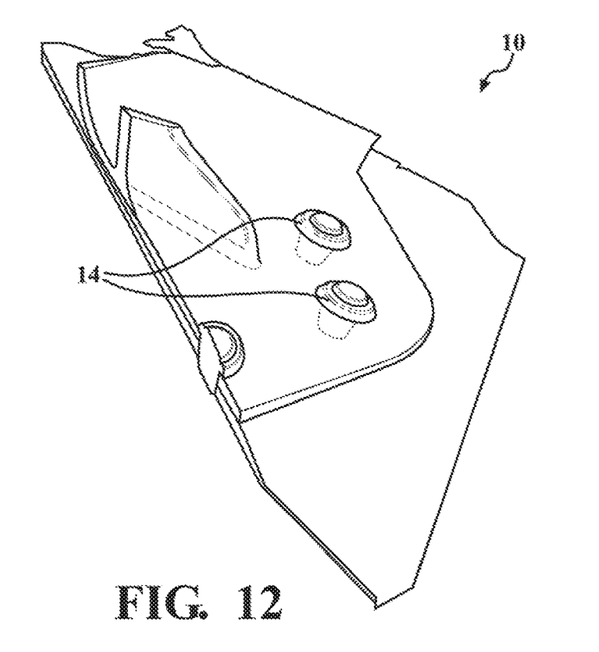

The presence of cracks, if any, the interlock $S_H$, the minimum thickness $T_{min}$, and the overall structure of the assembly 10 can be determined based on the x-ray images of the assembly 10 generated by the system and method. In other words, the resolution of images generated by the method is great enough to determine the presence of cracks, if any, the interlock $S_H$, the minimum thickness $T_{min}$, and the overall structure of the assembly 10. For example, the cross-sectional views of the assembly 10 shown in FIGS. 6-10 are obtained by the high energy x-rays, without having to cut the assembly 10. In FIG. 10, the interlock $S_H$, minimum thickness $T_{min}$, the button height H, the slug 26, the head 16 and base (leg) 18 of the rivet 14, the diameter D of the head 16, the top component 12a, and the bottom component 12b can be identified. The values for the interlock $S_H$, minimum thickness $T_{min}$, and the button height H can be obtained based on the diameter D of the head 16 of the rivet 14, which is a known value determined prior to joining the components 12a, 12b.

It should be appreciated that the foregoing description of the embodiments has been provided for purposes of illustration. In other words, the subject disclosure it is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varies in many ways. Such variations are not to be regarded as a departure from the disclosure, and all such modifications are intended to be included within the scope of disclosure.

The invention claimed is:

1. A method of inspecting an assembly including at least a first component and a second component joined by a rivet, the method comprising:
   scanning a portion of the assembly which includes the rivet joining the first component to the second component with computerized tomography (CT),
   generating a plurality of x-ray images of the portion of the assembly which includes the rivet, and combining the x-ray images together to form a combined image, and identifying a minimum thickness of the assembly based on the combined image, the minimum thickness being a distance between a bottom end of the rivet and a lowermost exterior surface of the second component.

2. The method of claim 1, wherein the scanning step includes emitting the x-rays at an energy level of at least 200 kV.

3. The method of claim 2, wherein the emitting step includes emitting the x-rays with a current of at least 200 milliamp (μA).

4. The method of claim 1, wherein the combined image has a resolution of at least 150 micrometers.

5. The method of claim 1, wherein the combined image has a resolution of at least 200 micrometers.

6. The method of claim 1 including identifying the presence of cracks in the portion of the assembly which includes the rivet based on the combined image.

7. The method of claim 1, wherein the rivet includes a head and a base, the head rests on a top surface of the first component, and the base extends through the first component and through a portion of the second component.

8. A method of inspecting an assembly including at least a first component and a second component joined by a rivet, the method comprising:
   scanning a portion of the assembly which includes the rivet joining the first component to the second component with computerized tomography (CT),
   generating a plurality of x-ray images of the portion of the assembly which includes the rivet, and combining the x-ray images together to form a combined image, wherein the rivet includes a head and a base, the head rests on a top surface of the first component, and the base extends through the first component and through a portion of the second component; and including the step of identifying an interlock present in the assembly based on the combined image, the interlock being a radial distance between a top end of the base and an outermost portion of the base of the rivet.

9. The method of claim 8 including the step of identifying a minimum thickness of the assembly based on the combined image, the minimum thickness being a distance between a bottom end of the rivet and a lowermost exterior surface of the second component.

10. A system for inspecting an assembly including at least a first component and a second component joined by a rivet, the system comprising:
    a source of x-rays and an x-ray detector,
    the source of x-rays emitting the x-rays toward a portion of the assembly which includes the rivet at an energy level of at least 200 kV,
    wherein the system generates x-ray images of the portion of the assembly which includes the rivet and combines the x-ray images to form a combined image,
    the system identifies a minimum thickness of the assembly based on the combined image, and the minimum thickness is a distance between a bottom end of the rivet and a lowermost exterior surface of a second component.

11. The system of claim 10 including a mounting unit disposed between the source of x-rays and the x-ray detector, the mounting unit holding the assembly.

12. The system of claim 10, wherein the combined image has a resolution of at least 150 micrometers.

13. The system of claim 10, wherein the system identifies the presence of cracks in the portion of the assembly which includes the rivet based on the combined image.

14. The system of claim 10, wherein the source of x-rays emits the x-rays toward a portion of the assembly which includes the rivet at a current of at least 200 milliamp (μA).

15. The system of claim 10, wherein the combined image has a resolution of at least 200 micrometers.

16. The system of claim 10, wherein the rivet includes a head and a base, the head rests on a top surface of a first component, and the base extends through the first component and through a portion of a second component.

17. A system for inspecting an assembly including at least a first component and a second component joined by a rivet, the system comprising:
   a source of x-rays and an x-ray detector,
   the source of x-rays emitting the x-rays toward a portion of the assembly which includes the rivet at an energy level of at least 200 kV,
   wherein the system generates x-ray images of the portion of the assembly which includes the rivet and combines the x-ray images to form a combined image, wherein the rivet includes a head and a base, the head rests on a top surface of a first component, and the base extends through the first component and through a portion of a second component; and the system identifies an interlock present in the assembly based on the combined image, the interlock being a radial distance between a top end of the base and an outermost portion of the base of the rivet.

18. The system of claim 17, wherein the system identifies a minimum thickness of the assembly based on the combined image, and the minimum thickness is a distance between a bottom end of the rivet and a lowermost exterior surface of a second component.

* * * * *